United States Patent [19]

Chow et al.

[11] Patent Number: 4,968,148

[45] Date of Patent: Nov. 6, 1990

[54] SINGLE SOURCE MULTI-SITE PHOTOMETRIC MEASUREMENT SYSTEM

[75] Inventors: Calvin Y. H. Chow, Portola Valley; Gillian M. Humphries, Los Altos; Viola T. Kung, Menlo Park; Michael M. Lacy, Ben Lomand; Paul Hayter, Los Altos, all of Calif.

[73] Assignee: Molecular Devices Corporation, Palo Alto, Calif.

[21] Appl. No.: 199,100

[22] Filed: May 26, 1988

Related U.S. Application Data

[63] Continuation-in-part of Ser. No. 901,445, Aug. 28, 1986, abandoned, which is a continuation-in-part of Ser. No. 782,635, Sep. 30, 1985, abandoned, which is a continuation-in-part of Ser. No. 597,135, Apr. 5, 1984, Pat. No. 4,591,550, which is a continuation-in-part of Ser. No. 585,334, Mar. 1, 1984, abandoned.

[51] Int. Cl.[5] .................... G01N 21/31; G01N 21/59
[52] U.S. Cl. .................................. 356/427; 356/436; 356/440
[58] Field of Search ............... 356/427, 440, 426, 428, 356/436; 250/576

[56] References Cited

U.S. PATENT DOCUMENTS

| | | |
|---|---|---|
| 3,447,906 | 6/1969 | Zimmerli . |
| 3,488,156 | 1/1970 | Good et al. . |
| 3,628,872 | 12/1971 | Miranda . |
| 3,697,185 | 10/1972 | Kassel et al. . |
| 3,855,868 | 12/1974 | Sudvaniemi . |
| 3,960,497 | 6/1976 | Acord . |
| 4,004,150 | 1/1977 | Natelson ............................ 250/576 |
| 4,026,666 | 5/1977 | Holmes . |
| 4,027,979 | 6/1977 | Komarniski . |
| 4,043,756 | 8/1977 | Sommervold . |
| 4,058,736 | 11/1977 | Takahashi et al. .................. 250/573 |
| 4,063,816 | 12/1977 | Itoi et al. . |
| 4,144,030 | 3/1979 | Suovaniemi ......................... 356/246 |
| 4,171,909 | 10/1979 | Kramer et al. ....................... 356/73 |
| 4,240,751 | 12/1980 | Linnecke et al. .................... 356/409 |
| 4,245,043 | 1/1981 | Lund .................................... 435/33 |
| 4,265,544 | 5/1981 | Banno et al. ........................ 356/427 |
| 4,290,997 | 9/1981 | Suovaniemi ..................... 356/246 X |
| 4,367,043 | 1/1983 | Sweet et al. ........................ 356/338 |
| 4,397,560 | 9/1983 | Andresen ............................ 356/440 |
| 4,431,307 | 2/1984 | Suovaniemi ........................ 356/246 |
| 4,447,150 | 5/1984 | Heinemann .......................... 356/41 |
| 4,448,534 | 5/1984 | Wertz et al. ........................ 356/435 |
| 4,456,380 | 6/1984 | Kondo et al. ....................... 356/418 |
| 4,459,024 | 7/1984 | Gergely ............................... 356/342 |
| 4,477,190 | 10/1984 | Liston et al. ....................... 356/418 |
| 4,482,251 | 11/1984 | Saylor ................................. 356/418 |
| 4,498,782 | 2/1985 | Proctor et al. ...................... 356/440 |
| 4,528,159 | 7/1985 | Liston ............................. 356/244 X |
| 4,536,369 | 8/1985 | Sakurada et al. ............... 356/433 X |
| 4,591,550 | 5/1986 | Hafeman et al. ...................... 356/4 |

FOREIGN PATENT DOCUMENTS

| | | |
|---|---|---|
| 0025350 | 9/1980 | European Pat. Off. . |
| 55-156840(a) | 6/1980 | Japan . |
| 2073930 | 10/1981 | United Kingdom . |

OTHER PUBLICATIONS

Masson et al., Methods in Enzym. (1981) 74:106–112.
Chen et al., Clin. Chem. (1984) 30:1446–1451.
Siezak et al., J. of Immun. Methods (1983) 65:83–95.
Karjalainen et al., J. of Physics E. (1974) 7:241–243.
Rook et al., J. of Immun. Methods (1981) 40:109–114.
Harris, IBM Tech. Disc. Bull. (1970) 12:1492.
Luderus, IBM Tech. Disc. Bull. (1973) 15:3577.
Hamrick et al., IBM Tech. Disc. Bull. (1961) 4:85.
Johnson, IBM Tech. Disc. Bull. (1971) 13:3430.
Kahwaty, IBM Tech. Disc. Bull. (1977) 19:4299–4300.

Primary Examiner—Vincent P. McGraw
Attorney, Agent, or Firm—Allegretti & Witcoff, Ltd.

[57] ABSTRACT

A multibeam photometric measuring device includes a single light source along with a filter assembly for passing only a desired band of wavelengths and an optical system for suitably focusing light from the light source. Light is transmitted individually to each of a plurality of sites disposed on a multi-well sample plate. Enhancement of color distribution is provided by automatic agitation of the reacting agents within the sample wells before a reading is taken at each of the sampling intervals of a kinetic measurement sequence.

30 Claims, 7 Drawing Sheets

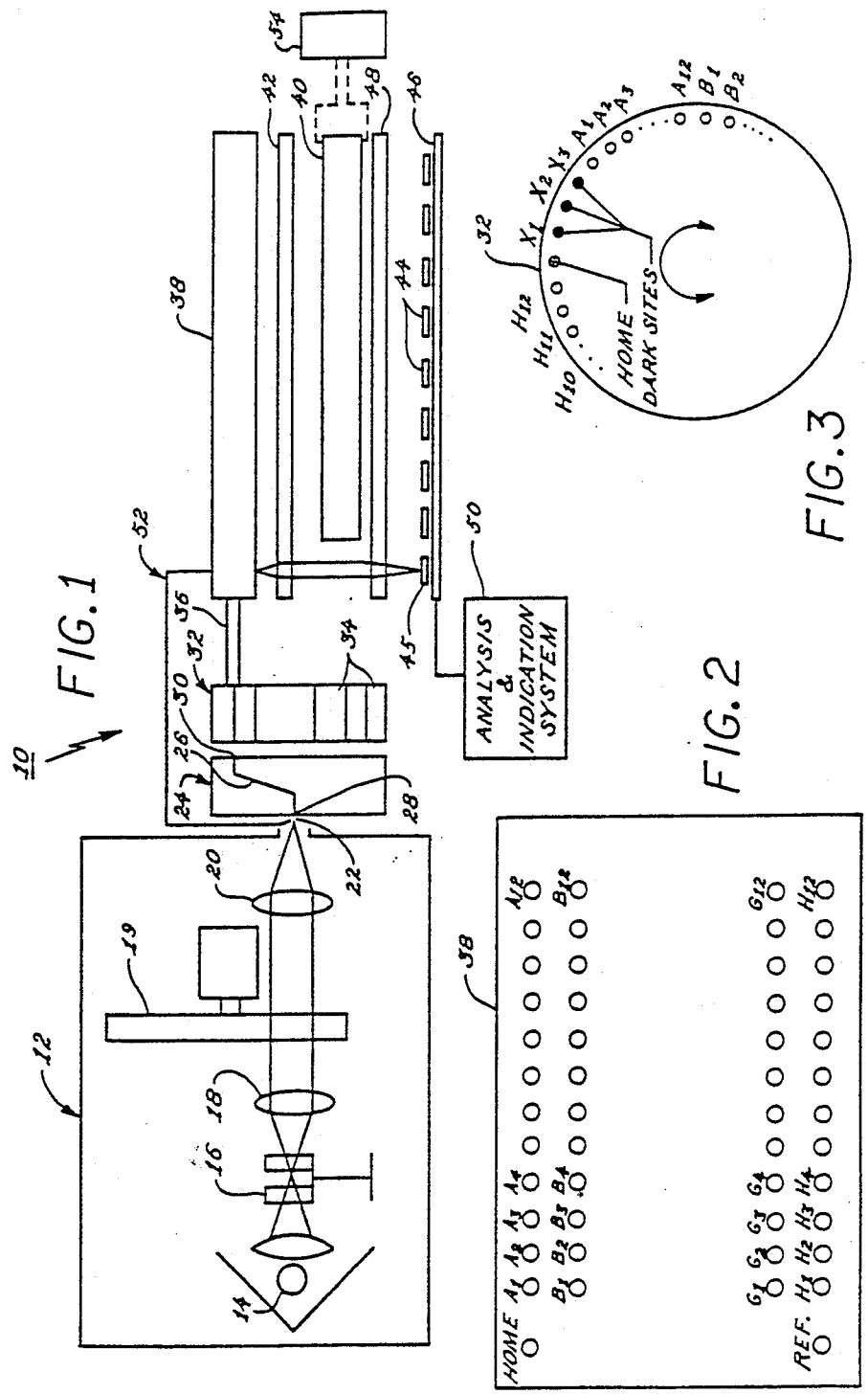

SINGLE SOURCE MULTI-SITE PHOTOMETRIC MEASUREMENT SYSTEM

CROSS-REFERENCE TO RELATED APPLICATION

This application is a Continuation in Part of co-pending application serial number 901,445 filed Aug. 28, 1986, which is a Continuation in Part of co-pending U.S. patent application Ser. No. 782,635 filed Sept. 30, 1985, entitled "Rapid Solid State Multibeam Photometer for Microanalysis," which is a continuation in part of application serial number 597,135, filed Apr. 5, 1984, which in turn is a Continuation in Part of U.S. patent application Ser. No. 585,334, filed Mar. 1, 1984.

FIELD OF THE INVENTION

This invention generally relates to photometric devices for performing densitometric measurements on translucent sites. More particularly, this invention relates to an automatic scanning device using end-point and/or kinetic measurement techniques for measuring the optical density of a plurality of translucent samples in order to analyze their contents.

BACKGROUND OF THE INVENTION

A variety of techniques and devices are commercially available for the detection and measurement of substances present in fluid or other translucent samples by determining the light transmitivity of the sample. In particular, a number of photometric devices are capable of simultaneously performing individual assays on a plurality of liquid or other translucent samples. Such methods generally handle a multiplicity of samples by using "microplates" which contain a standard array ($8 \times 12$) of wells and which are made of an optically transparent material. The optical density of the samples is measured by determining attenuation undergone by light as it passes through the translucent samples, contained in the microplate wells, to conventional photodetecting means.

A widespread use of microplates is in the enzyme-linked immunosorbent assay (ELISA) technique which is used for detection and quantitation of an extensive range of substances and biological cells in academic research and biotechnology as well as for clinical testing. In such assays, molecules of a marker enzyme (such as alkaline phosphatase) are deposited on the bottom and part of the way up the sides of each of the wells of a microplate; each well having been assigned to interact previously, directly or indirectly, with a sample containing an analyte of interest. The number of marker enzyme molecules bound to each well of the plate is a function of the concentration of analyte in the sample of interest. Determination of the activity of the bound enzyme, therefore, permits detection or quantitation of the analyte.

For determination of fluid-phase enzyme activity, current techniques for both research and clinical applications employ kinetic analysis which involves measurement of the initial rate of enzyme-catalyzed, chromogenic reactions in the presence of excess of the enzyme substrate; a procedure which has several well-known advantages over the alternative "end-point" analysis method of allowing the enzyme to react with a chromogenic substrate for a fixed period of time and then making a single optical density measurement after quenching the enzymes. In kinetic analysis, multiple readings are made within the initial (typically linear) reaction period and the intervals between readings are necessarily short (typically less than 30 seconds). By using kinetic analysis, the introduction of errors caused by (a) differences in initial optical density and/or (b) loss of independence from substrate concentration, is substantially avoided. An example of such assays includes the use of NADA and NADP, as described for example in Lehninger, "Biochemistry, the Molecular Basis of Cell Structure and Function", Worth Publishers, Inc., New York, 1970. NADA and NADP ultraviolet light photometers are particularly useful in performing assays.

Currently available automated optical density measurement instruments for microplates typically function by mechanically moving either the multi-well microplate or the optical components themselves in order to successively perform assays of samples located at the plurality of individual assay sites. This requirement places a severe restraint on the time required to actually measure the transmittance in all wells of the microplate, thereby making large scale kinetic analysis assay applications impractical due to the extended sampling times. In part because of this, "end-point" analysis is employed for ELISA protocols read by current instruments.

A measurement system which is capable of reading a plurality of assay sites in sequence without relative physical movement of the microplate and the optical components is disclosed in Wertz et al. U.S. Pat. No. 4,408,534 which discloses the use of fiber optic transmission means with a single light source sequentially coupled to a plurality of optical fibers which transmit light to the measurement sites. However, the apparatus described in the Wertz patent uses a highly inefficient system for coupling light from the light source into the optical fibers, which in turn leads to a variety of potential problems for kinetic measurements of enzyme activity. For example, the Wertz apparatus requires a high power light source and the increased light intensity can adversely affect the chemical reactions in the assay sites by increasing the operating temperature of the measurement system non-homogeneously and hence altering the rates of reaction in different wells to a different extent. In addition, such systems are unduly complex because of the wide fluctuation in signal levels generated as a result of the reception of light at the photodetectors after it has passed through the sample sites; this prevents efficient utilization of the overall dynamic range of amplification for the signal amplifiers of the measurement system.

Another limitation of conventional microplate reading devices is their inability to make useful quantitative measurements for ELISA protocols performed in filter-bottom microplates. A principal problem is that the individual wells in such plates vary considerably in their initial optical density relative to air thereby introducing considerable error when endpoint measurements are taken. Kinetic analysis, on the other hand, is not affected by this type of problem.

Another major problem associated with conventional microplate reading devices, when used for assaying chromogenic reactions kinetically, is that they are subject to errors arising from erratic redistribution of the colored product as a result of phase separation and/or uncontrolled bulk movement of the aqueous phase of the sample during kinetic analysis. More specifically, in the case of ELISA protocols where the enzyme is bound to the plastic surface of the microplate wells (on the bottom and/or part way up the sides), the bound enzyme interacts with an unstirred aqueous phase layer which typically causes localized phase separation of the colored product of the enzyme reaction due to its high local concentration. This separation introduces an unquantifiable error and a degree of non-linearity into such kinetic measurements. Even in cases where the colored product remains in true solution erratic bulk movement of the aqueous phase leads to uneven redistribution of tee concentrated product and hence to an unquantifiable error.

SUMMARY AND OBJECTS OF THE INVENTION

It is a primary object of this invention to provide an automatic photometric device for multi-site kinetic and/or end-point densitometric assays, which is capable of accurately acquiring a large number of measurements in a relatively short period of time.

Another important object of this invention is to provide such a photometric measurement device which uses a single relatively low power light source leading to reduced ambient operating temperature and extended life.

Another object is to provide such a photometric device with convenient control over the accuracy with which the sensed signals for this measurement system are processed.

It is a related object of this invention to provide a photometric device of the above kind which does not require relative mechanical movement of the microplate and the optical components of the system in order to perform successive multi-site assays.

Another important object of this invention is to provide such a photometric device which, by virtue of its ability to perform kinetic analysis, is able to make quantitative measurements of enzyme activity in filter-bottom microplates.

Another important object of this invention is to provide such a photometric device which provides significantly enhanced color distribution in the assay of chromogenic reactions and is not subject to measurement errors arising from non-uniform distribution of the colored product in such chemical reactions.

It is also a related object of this invention to provide a measurement device of the above kind which is efficient, economical and convenient to use.

These and other objects are achieved according to the system of this invention by providing a photometric measurement device which includes a light assembly comprising a single modulated light source along with a filter assembly for passing only a desired band of wavelengths and an optical system for suitably focusing light from the light source. A plurality of light transmitting means accept light from the light source through an efficient light distribution arrangement and transmit the light individually to each of the plurality of sites disposed on a multi-well sample plate. The light transmitting means are in the form of optical fibers evenly distributed about t&'e axis of a fiber distributor. A fiber rotor arrangement is provided for sequentially connecting the collimated light source to each of the plurality of fibers disposed in the distributor. The arrangement effectively connects the light source to only one of the plurality of test sites at any one time.

Light passing through the wells of the sample plate is captured by discrete photodetector cells disposed on a one-to-one correspondence opposite the wells of the plate. A reference fiber links light from the light source to a separate photodetector to provide a reference light signal with which the sensed signals, as represented by the signal outputs of the photodetectors, are compared; the photodetector output signals are then adjusted to reduce or eliminate fluctuations due to variations in system conditions such as lamp aging, thermal effects on photodetectors, etc. The signals from the photodetectors are suitably multiplexed and processed by special circuitry which allows control over the accuracy with which the signals are processed on the basis of their instantaneous strengths as well as reference readings taken during initialization of the system. Appropriate sequencing of the plurality of optical fibers to quickly sample each of the sample sites, and the processing of the resulting sensed signals in order to provide an external indication of the various tested transmittance values, is performed under the control of a conventional digital signal processor.

Enhancement of the distribution of the color resulting from chromogenic reactions is provided by automatic agitation of the reacting agents within' the sample wells before a reading is taken at each of the sampling intervals of the kinetic measurement technique. This arrangement ensures uniform distribution of the color products resulting from chemical reactions and promotes homogeneity of the reacting agents, leading to more accurate transmittance readings and increasing the overall system efficiency. In addition, agitation increases the pH equilibration rate of an enzyme, for instance, substrate solution is added after the immobilized enzyme is washed with a washing solution (usually pH 7). If the pH of the substrate solution is significantly different from the washing solution (e.g., the commonly used substrate solution of alkaline phosphatase is pH 9 or 10), a lag phase of color development occurs due to the slow pH equilibration of the enzyme. Automatic agitation of reagent speeds up the pH equilibration and significantly reduces the lag phase.

Other objects, characteristics and advantages of the present invention will be apparent from the following detailed description taken in conjunction with the accompanying drawings.

BRIEF DESCRIPTION OF THE DRAWINGS

FIG. 1 is a simplified schematic representation of a photometric reading device according to the system of this invention;

FIG. 2 is an illustration of the disposition of the various optical fibers within a fiber manifold associated with the sample assay sites;

FIG. 3 is an illustration of the fiber distributor showing the various designated positions utilized to couple the light source to each of the plurality of optic fibers;

DESCRIPTION OF THE PREFERRED EMBODIMENT

Figure 1A:
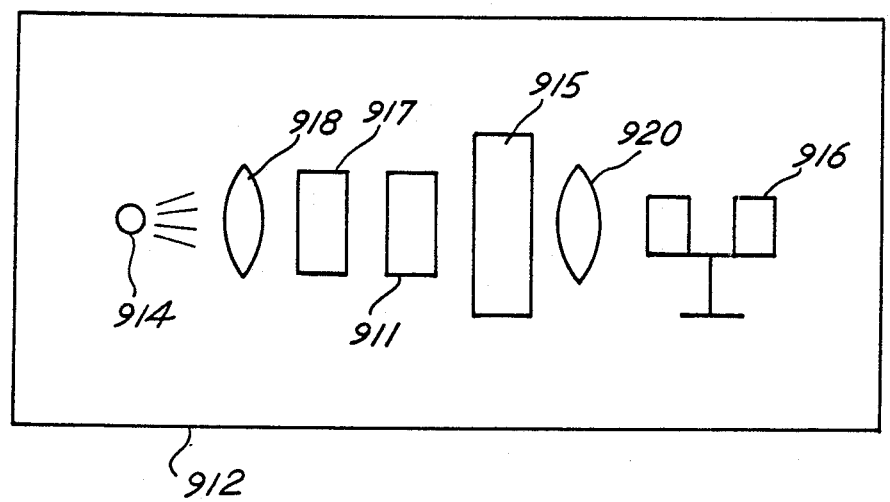
FIG. 1a is an alternative embodiment of light assembly 12 of FIG. 1.

While the invention will be described in connection with certain preferred embodiments, it will be understood that it is not intended to limit the invention to these particular embodiments. On the contrary, it is intending to cover all alternatives, modifications and equivalent arrangements as may be included within the spirit and scope of the invention as defined by the appended claims.

Referring now to the drawings, FIG. 1 is a simplified schematic representation of an exemplary kinetic measurement system 10 embodying the present invention. The system 10 includes a light assembly 12 capable of providing a finely focused reflected beam of light for coupling to the test or assay sites. The light assembly 12 comprises a single source of uniform, reflected and focused light 14 which, in the preferred embodiment, includes a tungsten-quartz bulb emitting light in a wavelength range of about 300 to 900 nanometers. The output of the light source 14 is passed through a chopper 16 which modulates the light at a fixed frequency which in the preferred embodiment is 800 hertz. In one embodiment, chopper 16 receives an input drive signal from a chopper control circuit (not shown), which also applies a signal to phase detector 126 (FIG. 4), as is described in more detail later. Preferably, to reduce noise, these signals from the chopper control circuit are carried over coaxial cable.

The modulated light from the chopper 16 is collimated through a lens 18 onto a filter wheel 19 which extracts light of a selected wavelength and bandwidth which corresponds to the wavelength at which the test samples exhibit light absorbency. The filtered light is passed through a lens 20 which receives the collimated light and focuses it onto a precise point 22 from which the light can be coupled to select fibers which conduct the light to the plurality of assay sites. In one embodiment, light from lens 20 is focused onto an optical fiber (not shown), which carries the light to optical fiber 26 of rotor 24. In an alternative embodiment, light assembly 12 is replaced with light assembly 912 of FIG. 1a. As shown in FIG. 1a, light assembly 12 includes lamp 914 which emits light including ultraviolet. Light assembly 912 also includes lens 918 which serves to collimate the light beam and infrared absorbing glass 917, which serves to remove undesired infrared energy which would otherwise heat and, over time, damage filters in the optical path Spectrum balancing filter 911 serves to balance the light intensity as a function of wavelength. In other words, since the light emitted from lamp 914 is richer in visible light than in UV, filter 911 tends to attenuate visible light more than UV, providing an output light beam which is more or less of equal intensity throughout the visible and UV spectrum. Interference filter 915, which may be one filter on a filter wheel containing a plurality of filters of different wavelengths, serves to select which wavelength of light is to be passed to the samples for the read operation. Lens 920 serves to focus the light beam onto an optical fiber, such as the optical fiber 26 within rotor 24 (FIG. 1), or an optical fiber (not shown) which delivers the light to optical fiber 26 within rotor 24. Between lens 920 and the optical fiber is located chopper 916. Naturally, any suitable arrangement of optical components is possible.

In one embodiment, light baffles (not shown) are utilized in order to prevent stray light from entering chopper 916, thereby preventing light of unselected wavelengths from being modulated by chopper 916 and being transmitted to the sample, preventing measurement error.

The kinetic measurement system 10 utilizes a highly efficient and structurally simple light coupling and transmitting mechanism. As shown in FIG. 1, the light exiting the light assembly 12 is directed to a light coupling arrangement which includes a cylindrical rotor 24 which is capable of being rotatably positioned accurately about its axis. The rotor 24 includes an optical fiber 26 having an input end 28 located at the center of the rotor 24 and coincident with the focal point 22 of the light output from the light assembly 12. The output end 30 of the fiber 26 is located near the periphery of the fiber rotor 24 so that as the rotor rotates the input end 28 of the fiber remains stationary with respect to the light assembly 12 while the output end 30 moves around a circular path. The rotor 24 thus permits efficient coupling of light from the light assembly 12 into selected ones of a plurality of light transmitting means which carry the light to corresponding assay sites.

The light output from the fiber 26 in the rotor 24 is received by a fiber optic distributor 32 containing a multiplicity of optical fibers 34 having their input ends arranged in a circular array. This circular array of fiber ends has the same radius as the location of the output end of the fiber 26 in the rotor 24 so that as the rotor 24 is indexed about its axis, the output end of the fiber 26 is brought into alignment with successive fibers 34 in the distributor 32. On the output side of the distributor 32, the fibers 34 are brought together to form a fiber bundle 36 which leads to a fiber manifold 38 which aligns each of the fibers 34 with one of the assay sites (to be described below).

The rotor 24 is indexed by means of a suitable stepper drive or other appropriate controllable displacement means so that it sequentially directs the light from the focal point 22 into different 34 of the bundle 36.

The use of the optical fiber coupling arrangement to couple light from the light assembly 12 to individual optical dibers 34 within the distributor 32 constitutes a significant advantage because of the efficiency of transmission associated with the mechanism. More specifically, the optical fiber 26 ensures that substantially all the collimated light from the light source 14 is coupled into a selected optical fiber 34 without any significant diffusion at the point of coupling at either end of the coupling fiber 26. Thus, light from the source 14 is coupled through the rotor 24 only into a selected one of the optical fibers 34 with minimal undesired coupling of light into optical fibers adjacent to the selected fiber. This highly efficient ocupling allows the use of a single light source with relatively low power capacity since a high percentage of light emanating from the source is transmitted to the site of measurement.

Of importance, the shape of the optical fibers within the rotor and the optical fibers connected to the distributor are maintained so as to prevent excessive loss in the light paths. This is accomplished by maintaining a suitable radius of curvature of the optical fibers In one embodiment, acrylic optical fibers are used, substantially preventing phosphorescence or fluorescence (emission of light other than that selected for application to the samples) when ultraviolet light is passed through the optical fibers.

The illustrated light source in FIG. 1 is a convenient and preferred form; however any light source or a plurality of light sources providing light of equal intensity and having the desired range of wavelength can be used.

At the site of measurement, light emanating from any of the optical fibers 34 located within the fiber manifold 38 is directed to a corresponding assay site on a sample plate 40 through an array of lenses 42 disposed between the manifold 38 and the sample plate 40. The sample plate 40 may be a conventional microplate having a series of wells, usually an array of 96 wells arranged in 8 rows having 12 wells each. The sample plate is preferably mounted in an area where the ambient temperature is regulated, e.g., by means of a fan, so as to present isothermal conditions about the sample plate This is important in minimizing inaccuracies from varying rates of reaction occurring at different sample sites as a result of a temperature gradient about the sample plate.

An array of photodetectors 44 is provided on a detector board 46 in the form of a matrix conforming to the positions of the wells located on the sample plate 40. A second lens array 48 is positioned beneath the sample tray 40 and serves as means for focusing light from each well of the sample plate 40, after the light has passed through the well. The lens arrays 42 and 48 are of the conventional type and include apertures (not shown) which function to direct the light towards the individual lenses and minimize diffusion of light into adjoining lenses and sample wells. The sample plate 40, or at least the bottom of each well in the sample plate, is translucent or transparent so that light coupled to a particular optical fiber within the fiber manifold 38 and then collimated onto a corresponding sample well penetrates the well and its contents, passes through the corresponding focusing lens disposed within the lens array 48, and reaches the corresponding photo-cell 44 located immediately below the sample well.

The photodetector 44 senses the intensity of the light passing through the corresponding sample well and produces an electrical output signal proportional to the intensity of light incident on its surface. Each of the photodetectors 44 provided on the detector board 46 functions in a similar manner and provides a signal which is proportional to the varying intensity of the modulated light impinging thereon. This varying intensity of the modulated light passing through the sample is caused by the varying transmittance offered by the sample as a chemical reaction progresses therein and alters its constituency. The resulting electrical signals from the photodetectors 44 are fed to an analysis and indication system 50 which processes the received signals and provides an external indication of the transmittance or optical density of each of the samples contained within the multiple wells of the sample plate 40.

The measurement system of FIG. 1 also includes a single reference optical fiber 52 positioned adjacent to the focal point 22 so that the fiber 52 receives light continuously whenever the light source 14 is energized, i.e., whenever any of the sample sites is being tested. The light emanating from the output end of the reference fiber 52 is coupled through air or an empty sample well to a separate photodetector 45 on the detector board 46, and provides a reference photodetector signal whose significance will be described in detail below.

The optic fiber distributor 32 also has an optical fiber designated as the "home" fiber which serves as a reference for determining the current position of the distributor 32 relative to the coupling rotor 24. The function of the home fiber will also be described in more detail below.

In order to promote uniform distribution of the color resulting from chromogenic reactions in the samples being measured, the measurement system of FIG. 1 is provided with means for agitating the chemical solutions contained within the plurality of wells of the sample plate 40. More specifically, as shown in FIG. 1, the sample plate 40 is attached to an agitating mechanism 54 which oscillates the tray in a manner that brings about a thorough mixing of the chemical solutions contained within the sample wells for approximately ten seconds. In an alternative embodiment, the multiple well microplate is oscillated over a distance of approximately 1/16 inch in a linear fashion at approximately 20 Hz for a period of approximately 125 milliseconds, followed by similar agitation at approximately 30 Hz for a period of approximately 125 milliseconds. These cycles repeat for approximately 3 seconds.

A common problem with conventional microplate readers, if used for kinetic analysis of ELISA, is that distribution of the color produced as a chromogenic reaction progresses may be uneven across the width of a sample well. Since kinetic optical density measurements generally involve the transmission of light through the central portion of a sample well, uneven distribution of color (e.g., due to color development on the walls or corners of a sample well) can severely distort the accuracy of the transmittance readings. Nonhomogeneous distribution of color in the samples can also produce significant variations in the measured values from one cell to another, even if similar chemical reactions are occurring in the cells, thereby making the transmittance measurements unreliable.

Although certain previous measuring techniques have suggested manual shaking of the microplate prior to reading, random diffusion of the color as the reaction progresses can introduce unpredictable, nonreproducible results into the otherwise generally linear variation of the kinetically measured optical density with respect to time; that is, the transmittance of the sample becomes dependent on the progressively non-homogeneous color distribution in the sample. This non-reproducibility cannot be overcome by shaking the microplate at the beginning of a kinetic reading cycle because, unlike conventional end-point measurement where the reaction is quenched prior to the measurement phase, kinetic reading involves measurement of optical densities while the reaction progresses unquenched. Because the color development continues as the reaction progresses, initial shaking, even though it provides a certain degree of linearity, is insufficient to produce a uniform distribution of color throughout the reacting solution and causes low precision measurements.

It has been found that agitation of the reaction agents immediately prior to each of the multiple readings taken within a kinetic reading cycle, in accordance with the present invention, significantly improves the measurement accuracy by ensuring a homogeneous distribution of the color product throughout the sample as the chemical reaction progresses. In the particular example illustrated in FIG. 1, such homogenous color distribution is achieved by oscillating the entire microplate before each reading is taken. The oscillatory movement agitates the reacting agents within each of the sample wells so as to prevent any localized separation of the colored products of the enzyme reactions. In this manner variation in the transmittance of the samples within the sample wells is maintained substantially linear with respect to time over an entire kinetic reading cycle.

In the particular embodiment shown in FIG. 1, the sample plate 40 is connected to an agitation mechanism 54 which comprises a motorized arrangement capable of imparting gentle oscillatory motion to the sample plate at a desired frequency of oscillation. According to one embodiment, the agitation mechanism 54 oscillates the sample plate with the same reversible drive motor generally used to control the position of the sample plate, by energizing the motor repeatedly in opposite directions at the desired rate of oscillation. Satisfactory results are obtained by oscillating the sample plate over a distance of about 1/16 of an inch at a frequency of about 20 Hz for approximately ten seconds. In an alternative embodiment, the multiple well microplate is oscillated over a similar distance in a linear fashion at approximately 20 Hz for a period of approximately 125 milliseconds, followed by similar agitation at approximately 30 Hz for a period of approximately 125 milliseconds, These cycles are then repeated, for example for approximately 3 seconds. The measurement system is programmed to oscillate the sample plate before each reading. The oscillation is followed by a short time delay before the start of the reading phase to allow the reacting solutions within the sample wells to settle. The delay interval prevents erroneous readings due to reflection and/or refraction effects arising from ripples caused by the agitation process. Typical time periods are 3 seconds from the agitation phase and 1 second for the delay interval.

The agitation need not be effected by mechanical means, as long as the objection of achieving homogeneous color distribution effect is realized. Other suitable agitation means, such as "ultrasonic" vibration inducement, may be used, depending upon the desired efficiency and the constituency of the reacting agents. Further, the oscillatory movement of the sample plate need not be limited to lateral or rotational movements parallel to the plane of the sample plate; vertical oscillation (up-and-down movement) can also be used satisfactorily as long as spilling of test samples can be avoided.

Referring next to FIG. 2, the fiber manifold 38 is shown in more detail, including the disposition of the various optical fibers across the lower surface of the manifold. It will be noted that this particular embodiment of this invention is designed for the sequential assaying of samples contained in a conventional microplate which has 96 test sites or wells arranged in 12×8 matrix. Accordingly, as shown in FIG. 2, the fiber manifold 38 has 96 fibers arranged in 8 rows A, 8, C, D, E, F, G and H, each row constituting of 12 fibers. For instance, the row A has 12 fibers ends $A_1$, $A_2$, $A_3$ $A12$.

Also located in the manifold 38 are the output ends of the reference fiber 52 and the "home" fiber. The arrangement of the 12 rows A-H and the separation between adjacent fibers corresponds exactly to the arrangement of the sample test sites in the sample plate used for the assay. Thus, light transmitted through a particular fiber is collimated directly onto the corresponding sample well and passes through to the corresponding photodetector, thereby generating an electrical signal having a magnitude proportional to the intensity of the light impinging on the photodetector.

FIG. 3 is a schematic representation of the fiber distributor arrangement showing the circular array of the input ends of the various fibers located in the fiber manifold 38. As shown, the distributor 32 carries the input ends of each of the 97 optical fibers disposed within the fiber manifold. These 97 fibers are arranged in a circular array around the distributor 32. The input end of the "home" fiber is located in a position preceding the first row A of optical fibers. Three opaque spots are located between the "home" fiber and the first fiber $A_1$ which corresponds to the first sample site to be assayed; these opaque spots serve to reference the start of a new assay sequence, as will be described below.

Figure 4:
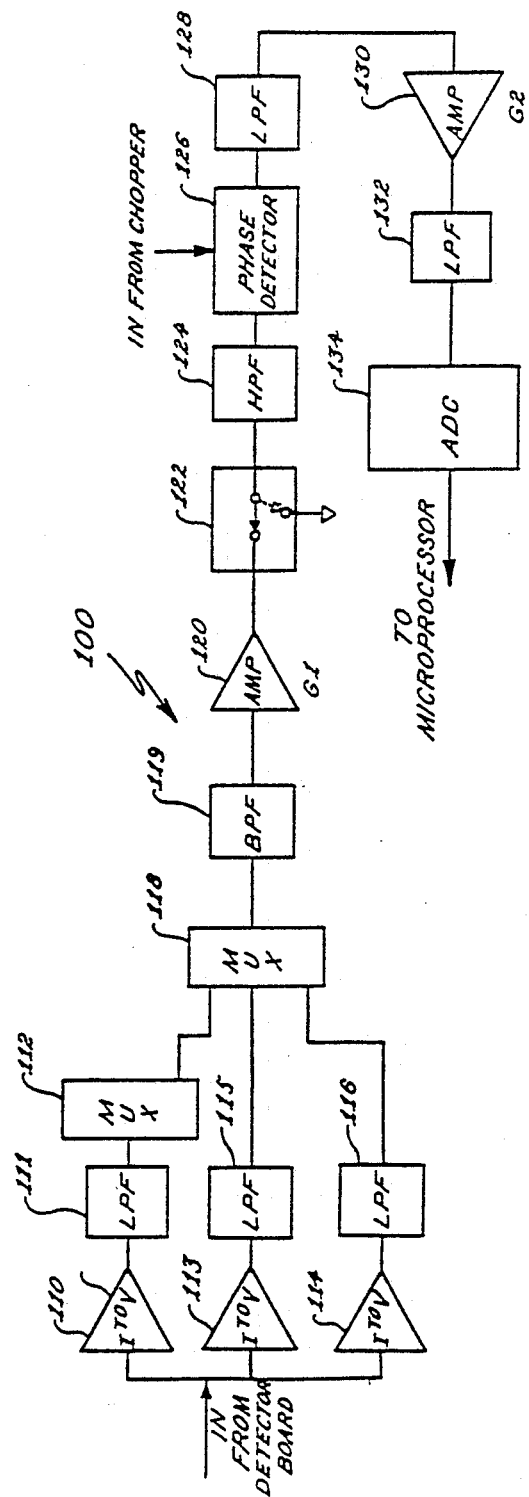
FIG. 4 is a simplified block diagram of the processing circuitry according to this invention.

Referring now to FIG. 4 there is shown a block diagram of the processing circuitry used for the analysis of the signals generated by the photodetectors 44. In the illustrative embodiment, the detector board 46 actually has 98 photodetectors 44, 96 of which correspond to the 96 sample sites of the sample plate 40 (FIG. 1), one of which receives light focused upon it from the reference fiber 52, and one of which receives light from the "home" reference fiber. It will be apparent that only a single reference photodetector is required if a single fiber is used to perform both the light and home reference functions. The signals generated by the 96 photodetectors for the sample sites are converted to a corresponding voltage form by a current-to-voltage converter 110. These signals are then passed through a band limiting low pass filter 1111 and subsequently to a multiplexer 112 which functions to controllably select desired ones of the 96 signals for further analysis according to a preprogrammed sequence.

The signals generated in response to light from the light reference fiber 52 and the "home" fiber are converted into their equivalent voltage form by current-to-voltage conversion units 113 and 114 and then passed through band limiting low pass filters 115 and 116, respectively. The outputs of the multiplexer 112 and the two low pass filter 115 and 116 are red to a second multiplexer 118 which functions to controllably select one of the three signals at its input for further analysis.

The "home" reference fiber provides a convenient means for locating the angular position of the fiber 26 in the rotor 24 relative to the fiber distributor 32. More specifically, the "home" reference fiber serves as a means for ensuring that the rotor 24 is positioned correctly so that the light output from the coupling fiber 26 is directed to the proper optical fiber in the distributor 32 to begin a sequential assaying process. Since any light entering the "home" reference fiber is transmitted directly to a dedicated "home" photodetector 44, the existence of a peak signal at the output of the "home" photodetector is an indication that the rotor 24 is positioned at a so-called "home" position where the coupling fiber 26 is aligned with the "home" reference fiber.

Any time a new assay is to be started, the measurement system first positions the rotor 24 at its "home" position. In order to accomplish this, the rotor 24 is rotated while monitoring the output of the "home" photodetector, until a peak output signal from the photodetector is detected. Since the position of the "home" reference fiber relative to the first optical fiber $A_1$ is a known factor (in this case, separated by the three opaque spots), subsequent alignment of the coupling fiber 26 with the fiber $A_1$ can be conveniently accomplished by stepping the rotor 24 through three consecutive positions.

The provision of the light reference fiber 52 serves as a calibration means by which the differences in sensed light intensity from one reading to another may be utilized for analysis of sample transmittance, thereby eliminating the effects of variations in the light output of the light source, system drifts and the like. More specifically, each time an assay is performed, the signal produced by the light reference fiber is measured before other start of the reading cycle. Then all subsequent signals produced by the photodetectors for the test sites are scaled relative to the signal initially produced by the light reference fiber. In this way, only actual changes in the transmittance of the liquid samples as a result of the chemical reactions occurring at the sample site are measured. Any localized differences in intensity such as those resulting from fluctuations in light intensity from the light source over the course of its lifetime, or premature readings taken before the light source or other system parameters have had a chance to stabilize, are disregarded.

Since the "home" reference fiber is coupled directly to the corresponding photodetector, it can also be conveniently used as reference light reading source and can effectively provide all functions performed by the light reference fiber as described earlier, in addition to providing a reference for determining the position of the fiber rotor 24 relative to the fiber distributor 32.

Returning now to FIG. 4, the signal selected by the multiplexer 118 is passed through a conventional bandpass filter 119 with a reasonably large bandwidth centered about the frequency at which the chopper 16 modulates the light passing through it (e.g., 800 hertz). The bandwidth of the bandpass filter 119 is selected to be sufficiently large to accommodate the fluctuation in signal settling time that occurs as a result of rapid readings being performed on the sample plate. The band-limited output of the filter 119 is then fed to a variable gain amplifier 120 whose function will be described below.

The output of the amplifier 120 is fed to a two-way switch 12 which in its normally closed position provides a direct electrical connection from the amplifier 120 to the subsequent portion of the processing circuitry. When the two-way switch 122 is open, the preceding portion of the measurement system is cut off and the switch 122 serves as a short circuit to ground to allow measuring the signal generated only by the rest of the processing circuitry. Thus, the switch 122 serves as a means for determining the "dark current" flowing through the processing circuitry in the absence of any light passing through the fiber distributor 32. This dark current measurement is free from distortions and noise from sources preceding the two-way switch 122, because the section of the processing circuitry in which the current is measured is totally isolated from the rest of the measurement circuitry. The significance of taking such readings while the circuit is isolated from the light source will be described below.

From the two-way switch 12, the output signal is passed through a high pass filter 124 which in combination with the low pass filters 111, 115 and 116 provides secondary bandpass characteristics to the processing circuitry. The output of the high pass filter 124 is fed through a phase detector 126 which in conjunction with a reference input from the light source chopper 16 and a low pass filter 128 functions to extract a direct current signal corresponding to the alternating current resulting from the modulating effect of the chopper 16. More specifically, the phase detector 126 effectively inverts either the positive or the negative portions of the alternating output signals from the detector board 46 on the basis of the timing input provided from the chopper 16. The average value of the resulting signal represents the DC equivalent of the alternating signal. To extract this average value, the output of the phase detector 126 is fed through a low pass filter 128. The filter characteristics of low pass filter 128 can have any suitable bandwidth in order to filter out undesired noise and provide a signal for measurement which is representative of the optical density of the sample being measured. In one embodiment of this invention, low pass filter 128 has a cutoff frequency of approximately 225 Hz; in another embodiment of this invention, low pass filter 128 has a cutoff frequency of approximately 53 Hz.

The output signal from the low pass filter 128 is fed to a second variable gain amplifier 130 which is a high precision amplifier providing a series of well defined gain settings. The operation of the variable gain amplifier 130 in conjunction with the first variable gain amplifier 120 in providing controllable accuracy and increased dynamic range for the processing circuitry of this invention will be described in detail below. The output of the amplifier 130 is passed through a low pass filter 132 and then on to an analog-to-digital converter 134 which functions to translate the amplified analog signal into its corresponding digital form. The digital signals produced by the analog-to-digital converter 134 are then fed to a conventional digital microprocessor system which performs a series of mathematical calculations and comparisons required to determine the optical density of the samples on the basis of a predefined algorithm. The same digital microprocessor system is also used to regulate the sequential scanning of the plurality of test sites, the different multiplexing arrangements, and all related processing circuit functions.

According to a feature of this invention, the measurement system is made more efficient and economical by effectively augmenting the dynamic range of the analog-to-digital converter (ADC) used to represent the analog signals defining the processed values of the various signals produced by the photodetectors. The variable gain amplifiers 120 and 130 function to adjust the extent to which the processed signals are amplified in such a way that even when the signals vary over a wide range of amplitudes, a major portion of the quantization levels of the analog-to-digital converter is utilized without exceeding its original dynamic range. The actual operation of the amplifiers will be clarified by considering the case where the ADC 134 in FIG. 4 having a 12-bit capacity so that the total number of quantized output levels is 4096, ranging from 0 to 4095. As the wavelength of light extracted (by the filter wheel 19 of FIG. 1) from the light emanating from the light source changes, the intensity of the resulting light also varies. This, in combination with variations in light transmission characteristics form one optical fiber to another and the frequency response characteristics of the photodetectors themselves, as well as changes in transmittance due to chemical changes in the samples, can produce signals whose amplitudes vary over a significant range.

In order to ensure that the signal with the largest possible amplitude does not result in an output value that exceeds the range of the ADC, it is conventional to use a low gain amplifier. However, the disadvantage associated with such an arrangement is that the low gain amplifier produces a low level digital output in cases where the intensity of light received at the photodetectors produces a relatively weak sensed signal, thereby utilizing the dynamic range of the ADC very inefficiently. Conventional recourse in such situations has been to upgrade the system by using an ADC with a higher bit-processing capacity, which significantly adds to the overall system cost.

According to this invention, the variable gain amplifiers 120 and 130 initially process the incoming signal at very low gain settings. The resulting digital output is then compared with the maximum possible value of the ADC output in order to determine the maximum possible gain to which the incoming signal may be subjected without exceeding the maximum digital output value of the ADC. For instance, if an input signal produces an ADC output of about 50 ($50_{10}$) or ($110010_2$) at the initial gain setting (which are normally a gain of 1) of amplifiers 120 and 130, the system compares this count value to the maximum count value possible with the ADC which, in the case of the 12-bit ADC, is 4095 and determines the extent to which the signal may be safely amplified so that the digital output falls within the maximum count value.

A safety margin of about 10% is built into this dynamic ranging process by performing the above comparison not on the basis of the maximum output value of the ADC but instead by comparison with a value that is roughly 90% of the maximum output. For the 12-bit supply ADC, the actual count of 50 would hence be divided into a safety-adjusted maximum output of 3686 counts to give a desired amplification factor of about 74. Subsequent to this determination, the gain settings of the variable gain amplifiers are adjusted to closely approximate the desired gain factor. The above arrangement thus allows maximum utilization of the dynamic range of the measurement system, regardless of variations in the relative strengths of the signals generated by the photodetectors.

According to this invention, the gain G1 of the first variable gain amplifier 120 is adjusted on the basis of the signal derived from light being transmitted through air, whereas the gain G2 of second variable gain amplifier 130 is adjusted on the basis of the signals derived from the sample site photodetectors. The actual sequence of operations involved in the adjustment of gain settings for the variable gain amplifiers as well as the overall method of operation of the measurement system will now be described below with reference to FIG. 5.

Figure 5:
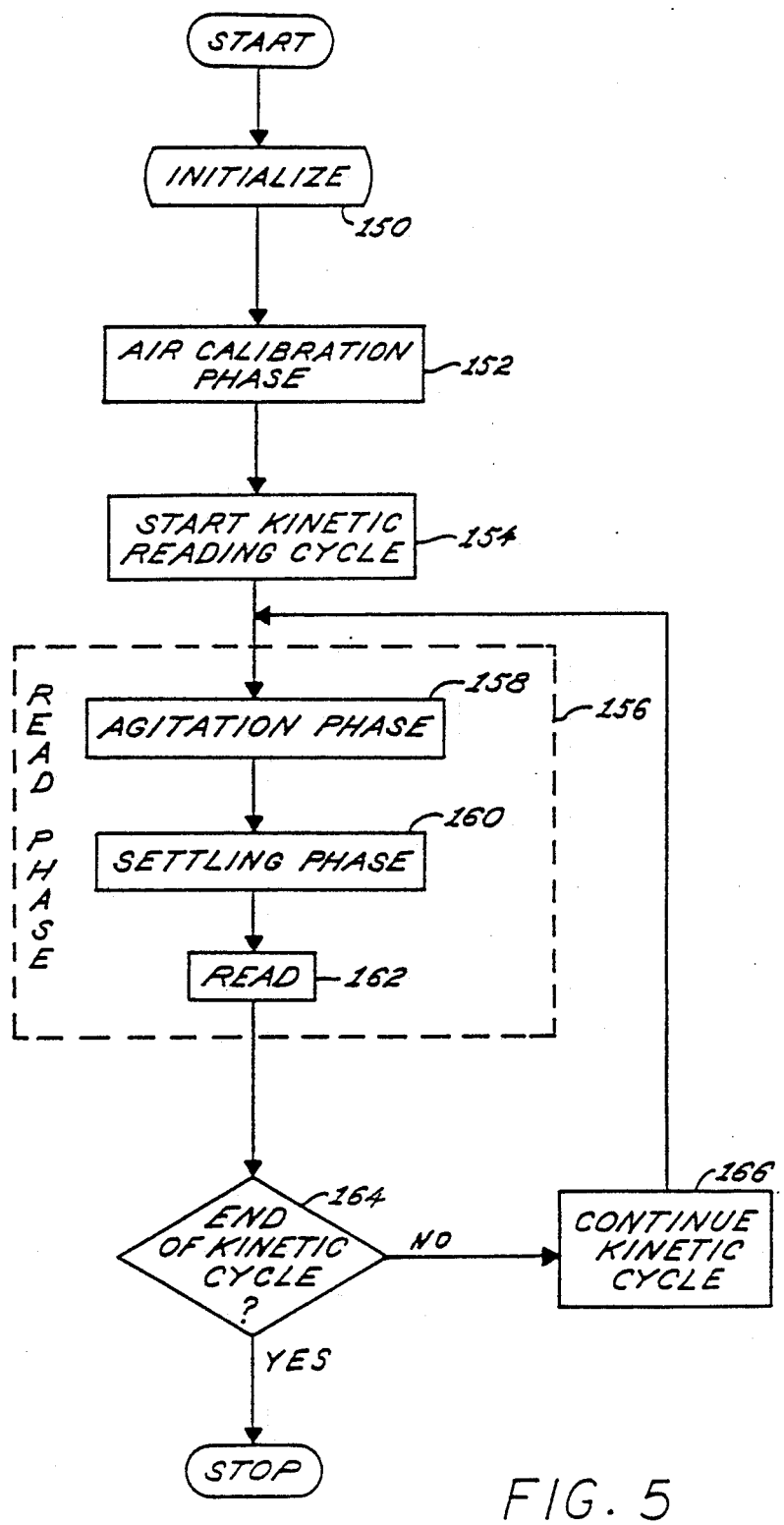
FIG. 5 is a flow chart representing the general sequence of operations involved in a typical sequential scan of the ample plate according to the illustrative measurement system.

FIG. 5 is a flow diagram of the general sequence of operations involved in a typical sequential scan according to the system of this invention. The sequence begins at step 150 where the various system variables, such as the number of readings to be made within the kinetic reading cycle and the time at which they are made, duration of agitation, the duration of the delay following the agitation phase, etc., are initialized. At step 152, the air calibration phase is carried out by performing a reading upon each of the sample wells through air. Measurements made during the air calibration phase are performed with a unity gain setting G2 for the second variable gain amplifier 130 and the gain G1 of the first variable gain amplifier 120 is optimized for the maximum dynamic range of the analog-to-digital converter. The various steps and measurements undergone as part of the air calibration phase 152 will be described in detail below.

The air calibration phase 152 is followed by step 154 where a kinetic reading cycle is initiated upon the basis of the initialization data provided to the measurement system as part of step 150. The kinetic reading cycle 154 includes the execution of the agitating, delay and reading steps at each of a series of pre programmed discrete time intervals at which optical density readings are to be taken for the particular samples being measured. It will be apparent that, in the case of end-point analysis, the reading cycle will comprise the execution of the above steps only at a single time interval. In one embodiment of this invention, the number of data points read is held to a reasonable number even when the length of the assay is long. In this embodiment, at the start of an assay data points are taken in relatively rapid succession (typically approximately 5 seconds, or 8 seconds when 3 seconds of agitation is utilized, between subsequent reads of a single sample well), while later in the assay the time between subsequent reads of a single sample well is increased. In this manner, when performing assays on chemistries which are rapidly changing in optical density, a large number of data points per sample are taken in a short period of time, while for chemistries which are slowly changing optical density, a number of data points per sample are taken over a longer period of time. In one embodiment, the time between subsequent readings of a single sample increases logarithmically with time. This effectively increases the dynamic range of rates of reaction, with greater accuracy.

Step 156 is the read phase, which includes a series of three steps beginning with the agitation phase 158 during which the sample plate is vibrated for a pre-defined time interval. Subsequently, at step 160, the settling phase takes place during a pre-defined delay interval in which the oscillation mechanism is dormant and the reaction agents within all the sample wells of the sample are allowed to settle down for a pre-defined time interval before obtaining the actual signal readings. At step 162 the measurement system obtains the transmittance reading on all the wells of the sample plate. This step includes optimization of the gain setting G2 for the second variable gain amplifier 130 while maintaining the gain setting G1 of the first variable gain amplifier 120 at the optimized value determined during air reference. The sequence of events involved in the read step 162 will be described in detail below.

Following the read step 162, a check is made at step 164 to determine whether the system has completed the pre-defined kinetic reading cycle. If the answer at step 164 is no, step 166 continues the kinetic reading cycle. The read phase 156 is reiterated by the measurement system until the agitation phase and the accompanying delay and read sequences have been performed at each of the prescribed intervals of the kinetic reading cycle. If it is found at step 164 that readings have indeed been performed at all prescribed time intervals, the measurement system comes to a stop. This marks the end of the kinetic reading cycle.

The reading cycle has been described above only with respect to the sequence of operations undergone by the illustrative photometric measurement divide in obtaining the various light readings required to calculate the optical density at the sample sites. It will be understood that the microprocessor system which forms part of the analysis and indication system FIG. 1) processes the data resulting from the measurements as the reading cycle proceeds and initiates computation of optical density values (on the basis of a pre-defined algorithm as will be explained below) for those sample sites and time intervals for which required measurements have been completed.

The following definitions and symbols will be used in the ensuing description of the various operations carried out by the measurement system of this invention during the air calibration and read phases.

$OD_n$: The calculated optical density of a given sample well (where n varies from 1 through 96 in order to designate each of the 12 sample wells positioned along each of the 8 rows A through H of the microplate).

$W_n$ n The signal output of a photodetector corresponding to a given sample well containing the reacting sample.

G1: The adjustable gain of the first stage variable gain amplifier 120 (controllable by a set of gain multiplication factors including 1, 2, 4, 8, 16, 32, 64 and 128).

G2: The adjustable gain factor for the second stage variable gain amplifier 130 (adjustable by a set of gain multiplication factors including 1, 10 and 100).

$D_n$: The dark current reading taken with the two-way switch 122 of FIG. 4 in its open position, for a given sample well. This reading is taken with the first stage gain setting G1 set to 1 and at the same second stage gain setting G2 used to obtain the corresponding $W_n$ signal output.

$S.AIR_n$: The signal reading of a given sample well's air calibration taken with the secondary stage variable gain amplifier at a gain setting G2=1.

$D_{air}$: The dark current reading of an air calibration performed with the secondary stage gain setting G2=1.

$L.REF_{air}$: The light reference signal reading taken during an air calibration with the secondary stage gain setting G2=1.

$L.REF_{read}$: The light reference signal taken at the initiation of a READ cycle with the secondary stage variable gain setting G2=1.

$D_{read}$: The dark current readings taken at the beginning of a READ cycle.

Figure 6:
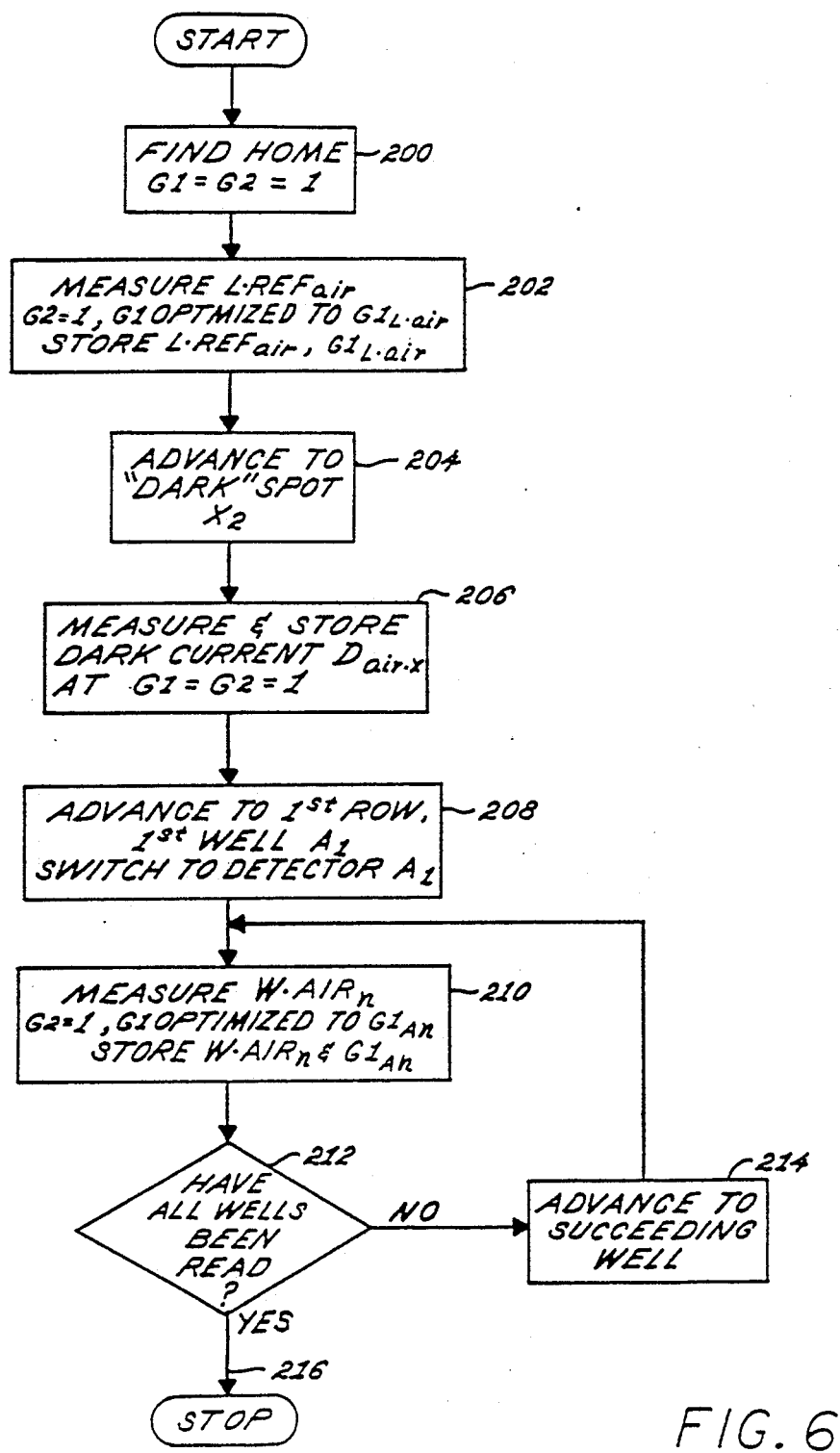
FIG. 6 is a flow diagram of the operating sequence undergone by the system as part of the air calibration phase.

Referring now to FIG. 6, there is shown a flow chart of the sequence of operations included within the air calibration phase of FIG. 5. At the first step 200, the measurement system positions the rotor 24 at the reference "home" position by sequentially displacing the rotor until the existence of a peak signal is detected at the output of the "home" reference photodetector. At this stage, the gain settings for both the first and second stage variable gain amplifiers 120 and 130 are set to unity. In an alternative embodiment, during the setting of the gain of amplifiers 120 and 130, the rotor is not located at a position corresponding to one of the three opaque spots on fiber distributor 32 since switch 122 is grounded.

The next step in the air calibration sequence is step 202 where the measurement system switches to either the photodetector for the light reference fiber or the photodetector for the home reference fiber in order to measure the light reference signal $L.REF_{air}$. This reading is measured with the gain G2 of the secondary stage variable gain amplifier set to unity and the gain G1 of the first stage variable gain amplifier optimized to provide the largest count value at the output of the analog-to-digital converter 134 (according to the safety-adjusted dynamic ranging procedure described above). Also at step 202, the measured reference signal value $L.REF_{air}$ and the optimized first stage gain setting $G1_{L.air}$ are stored in the memory of the microprocessor system for later use in the optical density calculations.

At the succeeding step 204, the rotor is displaced through a designated number of positions relative to the "home" position so as to locate the rotor at a position corresponding to one of the three opaque spots $X_1$, $X_2$ and $X_3$ on the fiber distributor 32. According to the preferred embodiment, the rotor is actually displaced by two positions relative to its home position so that the coupler comes to rest at a position corresponding to the opaque spot $X_2$. In this position, the opaque spot effectively blocks the coupling of any light from the coupling fiber 26 into any of the fibers in within the fiber manifold 32 and hence isolates the light source from the photodetectors.

At the succeeding step 206, the dual position dark current switch 122 activated and a dark current reading $D_{air}$ is taken with both the first and second stage gains G1 and G2 set to unity. The dark current reading $D_{air}$ represents the residual current flowing within the portion of the processing circuitry of FIG. 4 following the two-way switch 122. This value is subtracted from the signal reading of every sample well in order to provide a true representation of the transmittance value for the sample well at any designated time. Also at step 206, the measured dark current reading $D_{air}$ is stored in the system memory for later use in calculating the optical density.

At this stage, the measurement system is ready to perform air calibration readings on each of the sample wells. Accordingly, at step 208, the rotor 24 is advanced to the position $A_1$ corresponding to the first sample well of the multiple well plate, and the photodetector corresponding to the sample well $A_1$ is switched on. At the succeeding step 210, the air calibration signal reading $W.AIR_n$ for the sample well $A_1$ is taken with the gain G2 of the secondary stage variable gain amplifier set to unity and the gain G1 of the first stage variable gain amplifier optimized to a value $G1_A1$; the latter value represents the gain setting which allows the maximum safety-adjusted output from the analog-to-digital converter without exceeding its rated dynamic range. At the end of step 210, the measured signal reading $W.AIR_n$ (in this case $n=A_1$) and the optimized gain setting $G1_{Al}$ are stored in the memory.

At step 212, the microprocessor system checks to determine whether air calibration has been performed at each of the 96 sample well sites on the sample microplate. If the answer at step 212 is negative, step 214 advances the rotor to a position corresponding to the succeeding sample well site before reverting to the air calibration step 210. If the answer at step 212 is positive, i.e., air calibration has indeed been performed on all 96 sample well sites, it marks the end of the air calibration sequence at step 216. It will be noted that the entire air calibration sequence is performed with the sample plate in its retracted position, i.e., away from the photodetector board so that light from the fiber manifold 38 is transmitted directly to the photodetectors.

Figure 7:
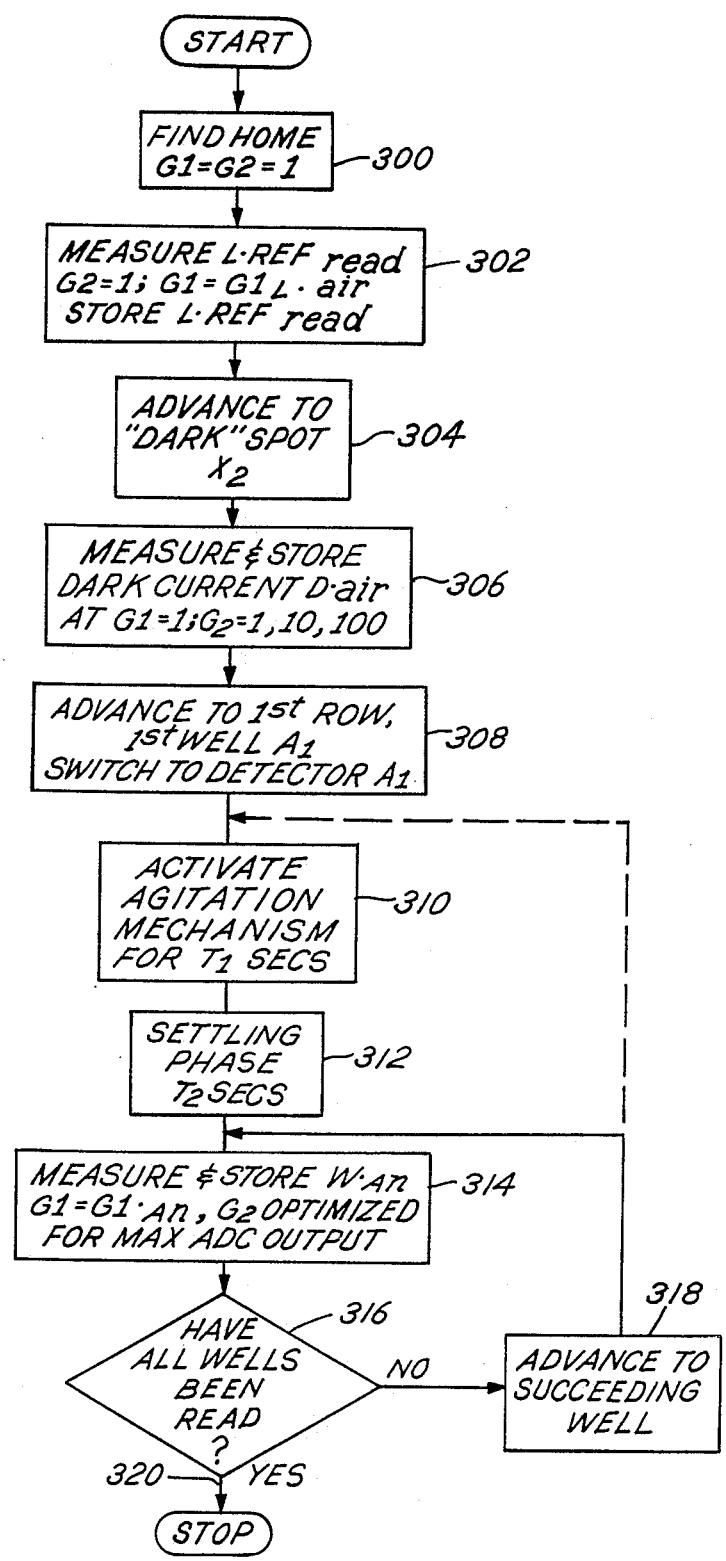
FIG. 7 is a flow chart representing the sequence of operations involved in performing the read phase on a sample tray, during an end-point assay; an FIG. 8. is a flow chart representing the sequence of operations involved in performing the read phase on a sample tray during a kinetic assay.

Referring now to FIG. 7, there is shown a flow chart of the sequence of operations undergone by the measurement system while performing the read phase during an end-point assay, i.e. an assay where, for example, samples are prepared in a multiple well micro plate and a predetermined time passed to allow the chemistries to develop, at which time (the "end-point") an assay of the samples is performed. It should be noted that before actual reading is performed on a sample plate, the measurement system proceeds through the air calibration phase with the sample plate in its retracted position. Prior to the start of a read phase, the sample plate is moved into its advanced position in preparation for the reading phase.

At the start of a reading operation (step 300 in FIG. 7), the measurement system locates the rotor at the "home" position. For this purpose, the signal from the "home" reference fiber photodetector is tracked by the processing circuitry with both the first and second stage variable gain amplifiers having their gains G1 and G2 set to unity.

Step 302 is then accessed, where a measurement of a light reference signal occurs. More specifically, the measurement system switches to the photodetector corresponding to the light reference fiber (or the photodetector corresponding to the home reference fiber if this fiber is being used to perform the functions of the light reference fiber), and a light reference signal L.RE-$F_{read}$ is taken with G2 set to unity and G1 optimized to its maximum value $G1_{L.air}$ according to the dynamic ranging procedure described above. Also as part of step 302, the measured L.REF$_{read}$ value is stored in the system memory for later use during calculations of optical density.

At the succeeding step 304, the rotor 24 is displaced through a designated number of positions to locate it at one of the three opaque spots $X_1$, X2 and X3 provided on the fiber distributor 32. More specifically, the rotor is stepped two positions relative to the home reference fiber so as to be located at the second opaque spot $X_2$.

The following step 306 actuates the dual position switch 122 and measures a series of dark current readings $D_{air.x}$ with the first stage variable he first stage variable gain G1 set to unity. A single reading is taken at each of the possible gain settings G2 (in this case 1, 10 and 100) of the secondary stage variable gain amplifier. The measured values of $D_{air.x}$ are also stored within the system memory as part of step 306.

At the succeeding step 308, the rotor is advanced to the first sample well position $A_1$. In addition, the system switches to the photodetector corresponding to the first sample well $A_1$ to begin the actual sequential reading cycle. The succeeding step 310 activates the agitation mechanism for a predesignated time interval $T_1$ to promote homogeneous color distribution as described above.

The agitation phase of step 310 is succeeded by a settling phase at step 312 during which the agitation mechanism is deactivated and the system dwells for a time interval $T_2$ to allow the agitated samples to settle down in preparation for performing transmittance readings upon them. The agitation phase at step 310 may entail displacement of the sample from its position between the fiber manifold and the photodetector board to permit oscillatory movement of the plate. Accordingly, the settling phase may actually take place during the time it takes to reposition the plate from its agitation position to its reading position. Immediately after agitation and the subsequent settling of the reacting samples within the sample plate, optical density readings are taken.

At step 314, the signal $W_{An}$ for the first sample well, i.e., $A_1$, is measured with G1 set to the corresponding stored gain value $GA_1$ determined as part of the air calibration (step 210 in FIG. 6). During this measurement, G2 is initially set to unity and then optimized to a value that produces the maximum safety-adjusted output value from the analog-to-digital converter of FIG. 2. Also, as part of step 314, the measured signal value $WA_1$ is stored within the system memory for use in calculation of the optical density for that sample well.

At the succeeding step 316, the microprocessor system performs a check to determine whether signal readings have been obtained for all 96 sample wells. If the answer at step 316 is negative, the microprocessor system advances the rotor to a position corresponding to the next sample well. At the same time, the processing circuitry switches to monitor the photodetector corresponding to the selected sample well. The system then reverts to step 310 and goes through the agitation, settling and read steps 310, 312 and 314 again. These three steps are reiterated until the check at step 316 produces a positive answer, indicating that signal readings have been obtained from all sample wells. This marks the end of the reading cycle at step 322.

In an alternative embodiment, shown by the dashed line in FIG. 7, following step 318 in which the rotor and photodetector circuitry advanced to the next well to be read, read step 314 is performed without repeating agitation step 310 and settling step 312. In this embodiment, a single agitation step 310 and settling step 312 are performed prior to reading all 96 wells on the microplate.

Figure 8:
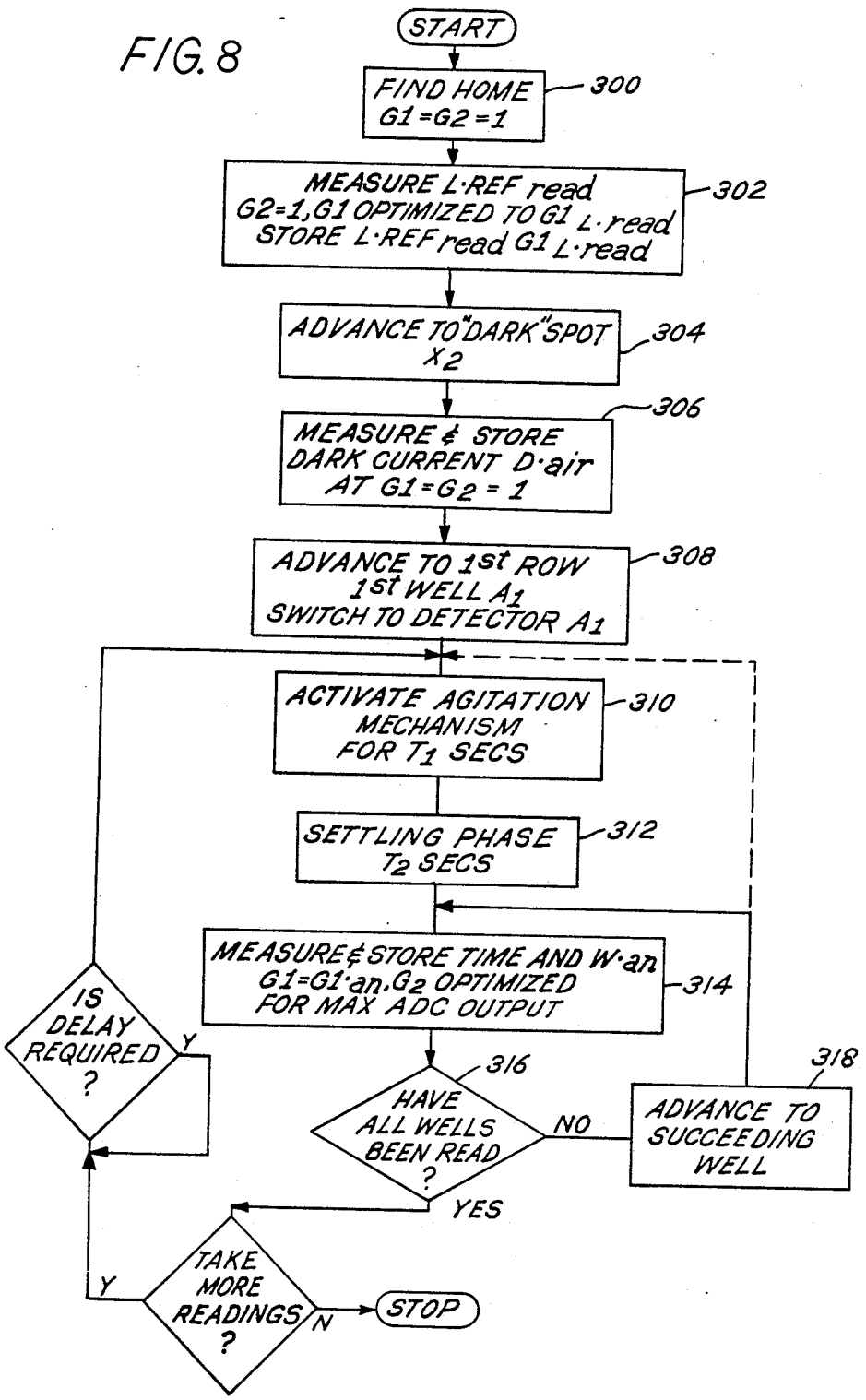

One embodiment of a sequence of operations to perform kinetic reading of samples is shown in the flowchart of FIG. 8. During kinetic reading of samples, a plurality of readings are taken at each sample, in order to determine the rate of chemical reaction at each sample over time. As shown in FIG. 8, the operation steps of the end-point assay of FIG. 7 are utilized in conjunction with an additional loop, which includes steps 322 and 324. Following a positive determination by step 316, i.e. that all wells have been read, step 322 determines if it is desired to take an additional set of readings for each well. If not, the operation is stopped. On the other hand, if it is desired to take an additional set of readings, step 324 is performed. Step 324 simply serves to provide a predetermined delay time between successive sets of readings. Such time delay may be a fixed time delay or, as previously described, may vary with time, for example by varying logarithmically with time. Following the time delay, if any, provided by step 324, step 310 et. seq. are again performed in order to obtain a complete set of readings for the 96 samples in the multiple well plate. In one embodiment, the agitation prior to the initial set of readings is performed for about ten seconds, and subsequent agitations, performed before each subsequent set of readings, is performed for about three seconds. If desired, for each sample, analysis of rate of reaction is terminated upon a change of optical density (for example a change of approximately 0.200 OD), thereby providing data points only for the substantially linear portion of the reaction of each sample.

It will be noted from the above description that for any given sample well designated by the letter n, the gain $G1_n$ for the first stage variable gain amplifier 120 is individually determined for each sample well during the air calibration phase, and then is maintained constant for all subsequent readings in that kinetic reading cycle. The value of G1 is not adjusted again until the next air calibration phase. The gain $G2_n$ for the second stage variable gain amplifier is set equal to unity for all air reference and light reference readings, so that the dynamic range of the second stage amplifier 130 is utilized only when actual transmittance readings are being taken, and not for air reference readings.

Once the optical parameters defined and described above with respect to FIGS. 6, 7, and 8 have been obtained by the measurement system for a given sample well, the calculation of the optical density $OD_n$ of the reacting sample contained within that sample well is calculated as:

$$OD_n = \text{LOG}_{10}[(W.\text{AIR}_n - D_{air})/(W_n - D_n)*$$
$$(L.\text{REF}_{read} - D_{read})/(L.\text{REF}_{air} - D_{air})*(G2_n)]$$

This equation represents the logarithmic value of the product of three separate quantities. The first quantity $(W.\text{AIR}_n - D_{air})/(W_n - D_n)$ is the ratio of the adjusted signal readings for a given sample well (1) without any sample and (2) with a sample. All readings measured by the processing circuitry of the microprocessor system are adjusted for any offset voltages generated by the analog-to-digital converter or other system offsets and drifts by taking into account the corresponding dark current readings, as indicated in the above equation for $OD_n$. For instance, the signal reading $W.\text{AIR}_n$ is normalized for dark current effect by subtracting from it the value $D_{air}$ of the corresponding dark current reading. Similarly, this signal reading $W_n$ is adjusted by subtracting from it the corresponding dark current reading $D_n$.

The second quantity $(L.\text{REF}_{read} - D_{read})/(L.\text{REF}_{air} - D_{air})$ is a measure of the ratio of the light reference readings obtained for a given sample well during the air calibration phase and the read phase. These two readings are also normalized on the basis of the corresponding dark current readings.

Finally, the third quantity $(G2_n)$ in the above equation accounts for the effect of the dynamic ranging procedure described above, i.e., this quantity accounts for the effects of amplification of the signal readings by the processing circuitry.

The application of the above equation to the parameters measured as part of the kinetic reading cycle results in a highly accurate optical density measurement because the equation takes into account the effects of system offset voltages as well as those resulting from localized differences in light intensity and measurement conditions from one kinetic reading cycle to another, or from one sample well to another.

In accordance with a further feature of this invention, the computation of the logarithms required to calculate the optical density readings is performed by storing all the required logarithmic values within the microprocessor system in the form of a look-up table and subsequently using the digitized output of the processing circuitry as an index to retrieve the appropriate logarithmic value. In previous systems, the output signals of the photodetectors of the detector board have been fed to a logarithmic amplifier to obtain the logarithmic values of the output signals. This technique is subject to a variety of problems and limitations because of the constant need to adjust the system for offset gains of the logarithmic amplifiers. In addition, any temperature drift in the computing hardware must be accurately tracked and appropriately compensated to retain the accuracy of computation. According to the present invention, the computation of the logarithmic values is made substantially more accurate and independent of the system hardware parameters by storing within the microprocessor system memory all possible logarithmic values that would be required by the system in order to compute the optical density readings.

More specifically, the look-up table contains logarithmic values corresponding to each of the possible output quantization levels for the analog-to-digital converter of the system (as shown in FIG. 4). Considering, for example, the case of a 12-bit supply analog-to-digital converter, the possible quantization levels range from 0 to 4095. This means that there are 4096 different values that a signal may take after it has been detected, processed and digitized. The logarithmic value corresponding to each of these 4096 possible values (except value 0, which denotes an error) are stored within a logarithmic look-up table which is contained within the ROM portion of the microprocessor system. The logarithmic look-up table is defined in such a way that the digitized output from the analog-to-digital converter serves as an address or index that points to the corresponding logarithmic value stored within the look-up table.

Because the look-up table is available within the microprocessor system memory, computation of the optical density becomes a simple matter of using the digitized output to extract the corresponding logarithmic value stored within the look-up table, and then performing simple mathematical subtractions.

According to yet another feature of this invention, the process of selecting a particular photodetector from the multiplicity of detectors on the detector board is simplified by use of a tiered parallel addressing scheme for the photodetectors. More specifically, the photodetectors are divided into a selected number of blocks, each block consisting of a plurality of photodetectors. Corresponding photodetectors in the various blocks are connected in a parallel fashion in such a way that if, for instance, the first photodetector in the first block is addressed, the measurement system also automatically addresses the first photodetectors in the remaining blocks.

Considering, for example, the case of a 96-well microplate, the detector board comprises 97 photodetectors (96 for the 96 sample wells and 1 for the "home" and light reference fiber). According to a preferred embodiment of this invention, the 96 sample-well photodetectors are divided into blocks consisting of 16 photodetectors each. The first block consists of the photodetectors $A_1$-$A_4$, $B_1$-$B_4$, $C_1$-$C_4$ and $D_1$-$D_4$, the second block consists of the photodetectors $A_5$-$A_8$, $B_5$-$B_8$, $C_5$-$C_8$ and $D_5$-$D_8$, the third block consists of the photodetectors $A_9$-$A_{12}$, $B_9$-$B_{12}$, $C_9$-$C_{12}$ and $D_{12}$, *fourth block consists of the photodetectors* $E_1$-$E_4$, $F_1$-$F_4$, $G_1$-$G_4$ and $H_1$-$H_4$, the fifth block consists of the photodetectors $E_5$-$E_8$, $F_5$-$F_8$, $G_5$-$G_8$ and $H_5$-$H_8$ and the sixth block consists of the photodetectors $E_9$-$D_{12}$, $F_9F_{12}$, $G_9$-$G_{12}$ and $H_9$-$H_{12}$. With this block configuration, the first photodetectors in all of the blocks, that is $A_1$, $A_5$, $A_9$, $E_1$, $E_5$ and $E_9$, are connected in parallel, and the rest of the photodetectors are connected in a similar fashion.

The addressing of individual photodetectors is considerably simplified since the same address is applicable to the selection of any one of the six photodetectors. Even though six photodetectors are turned on each time only one of them is to be actually monitored, the detectors within any given block are spaced sufficiently apart on detector board 46 so that undesired light scattering does not affect other photodetectors in the selected block. In other words, during illumination of a single well, light is scattered from that well and may impinge on photodetectors which are physically close to the photodetector associated with the single well being illuminated. However, since the other five photodetectors in the block containing the illuminated photodetector are not physically close, they will receive no scattered light and will not adversely affect the reading being taken from the photodetector associated with the illuminated well.

In one embodiment, a fan arrangement is used to maintain substantially constant temperature within the photometer and to ensure that any vapors are removed from the device, thereby preventing vapor condensation in the optical paths within the photometer. In one embodiment which utilizes such a fan arrangement, one or more baffled channels are used to permit air flow while preventing light from entering the photometer, thereby preventing adverse effects due to undesired light.

All publications and patent applications are herein incorporated by reference to the same extent as if each individual publication or patent application was specifically and individually indicated to be incorporated by reference. The invention now being fully described, it will be apparent to one of ordinary skill in the art that many changes and modifications can be made thereto without departing from the spirit or scope of the appended claims.

What is claimed is:

1. A multibeam photometric measurement device for measuring optical density of samples contained in a plurality of sample sites disposed on a multi-site assay plate, said device comprising:

a single light source adapted through coupling means to be selectively applied, according to a predetermined sequence, through selected ones of a plurality of light transmitting means to selected ones of said samples sites:

a plurality of photodetector means disposed on a detector board and positioned in relation to said assay plate in such a way that light transmitted through each of said sites is received by a corresponding photodetector;

means for simultaneously imparting mixing movement to said samples comprising means for imparting movement to said assay plate for a predetermined time before a reading is performed on a sample site; and means for analyzing the output of said photodetector means to determine and indicate the optical density of said sites.

2. As measurement device as in claim 1, wherein said light source provides ultraviolet light.

3. A measurement device as in claim 2 which further comprises a spectral balancing filter to filter light from said light means and provide light of substantially constant intensity over the visible and ultraviolet spectrum.

4. A measurement device as in claim 1 wherein said light transmitting means comprise optical transmission fibers and said coupling means comprises:

a fiber rotor including a rotor optical fiber receiving substantially all of said light at an input end transmitting it to an output end; and a fiber distributor including said plurality of transmission optical fibers disposed in a manner allowing each of said transmission optical fibers to be selectively coupled to the light coming out of the output end of said rotor fiber, said fiber rotor capable of being displaced in such a way that said optical fiber couples light from said source to successive ones of said transmission optical fibers and hence to successive ones of said sample sites.

5. A measurement device as in claim 4 which further comprises:

means for modulating the light source at a predetermined rate; and means for filtering light of a desired wavelength from said light source for application to said sample sites.

6. A measurement device as in claims 4 or 5 wherein said fibers comprise material which emits substantially no light of wavelengths other than that which it receives.

7. A measurement device as in claim 4 wherein said distributor also contains a first reference optical fiber directly coupling said light to a first reference photodetector on said detector board.

8. A measurement device as in claim 7 wherein said first reference fiber functions as a means for referencing the relative positioning of said fiber rotor with respect to said distributor.

9. A measurement device as in claim 7 wherein said first reference fiber serves as a light referencing means.

10. A measurement device as in claim 8 wherein said first reference fiber also serves as a light referencing means.

11. A measurement device as in claim 6 further including a second reference optical fiber directly coupling said light to a second reference photodetector disposed on said detector board and functioning as light referencing means.

12. A measurement device as in claims 7 wherein said assay plate comprises 96 sample sites disposed in an $8 \times 12$ matrix and said detector board comprises a corresponding $8 \times 12$ matrix of photodetectors in addition to a single photodetector corresponding to first reference fiber.

13. The apparatus of claim 4 wherein said means for analyzing comprises:

means for sequentially selecting the analog output signals of desired photodetectors for analysis;

means for converting said analog signals to their corresponding digital values;

means for amplifying said analog signals in such a way as to utilize a substantial portion of the dynamic range of said analog to digital conversion means;

means for storing precalculated values corresponding to said digitized values, accepting said digitized values and retrieving the corresponding stored precalculated value in response to each of said digital values; and means for processing said retrieved values in order to calculate the optical density of said samples.

14. A measurement device as in claim 13 wherein said photodetectors are divided into blocks, each consisting of a plurality of photodetectors, in such a way that photodetectors in said blocks are spaced substantially apart on said detector board, and the outputs of the photodetectors of each said block are connected together to yield a common output signal, whereby the output of a selected photodetector can be analyzed by selecting the common output signal for the block in which the photodetector lies.

15. A measurement device as in claim 14 wherein each of said blocks comprises 6 photodetectors.

16. A measurement device as in claim 13 wherein said means for analyzing further comprises means for analyzing that portion of said analog signal which is modulated at said predetermined rate.

17. A measurement device as in claim 14 wherein the distributor further comprises means for preventing light from being coupled into said light transmitting means, and said means for analyzing includes means for measuring any output from the analog to digital conversion means in the absence of light being coupled to the transmitting means.

18. A measurement device as in claim 1 which further comprises a drive motor for advancing and retracting said assay plate relative to said detectorboard.

19. A measurement device as in claim 18 wherein said drive means further serves for imparting said movement to said assay plate.

20. A photometric measurement device for measuring optical density of samples contained in a plurality of sample sites disposed on a multi-site assay plate, said device comprising:
a light source for applying light to selected ones of said sample sites;
photodetector means positioned in relation to said assay plate in such a way that light transmitted through each of said sites is received by said photodetector;
means for simultaneously imparting mixing movement to said samples comprising means for imparting movement to said assay plate for a predetermined time before a reading is performed on a sample site; and
means for analyzing the output of said photodetector means to determine and indicate the optical density of said sites, said means for analyzing comprising:
means for sequentially selecting the analog output signals of desired photodetectors for analysis;
mean for converting said analog signals to their corresponding digital values;
means for amplifying said analog signals in such a way as to utilize a substantial portion of the dynamic range of said analog to digital conversion means;
means for storing precalculated values corresponding to said digitized values, accepting said digitized values and retrieving the corresponding stored precalculated value in response to each of said digital values; and
means for processing said retrieved values in order to calculate the optical density of said samples.

21. A measurement system as in claim 20 wherein said means for imparting mixing movement to said samples comprises means for imparting movement to said assay plate.

22. A measurement device as in claims 20, or 24 wherein said light source provides ultraviolet light.

23. A measurement device as in claim 20 wherein said means for analyzing further comprises means for analyzing that portion of said analog signal which is modulated at a predetermined rate.

24. A photometric measurement device for measuring optical density of samples contained in a plurality of sample sites disposed on a multi-site assay plate, said device comprising:
a light source for applying light to selected ones of said sample sites;
photodetector means positioned in relation to said assay plate in such a way that light transmitted through each of said sites is received by said photodetector;
means for simultaneously imparting mixing movement to said samples comprising means for imparting movement to said assay plate for a predetermined time before a reading is performed on a sample site; and
means for analyzing the output of said photodetector means to determine and indicate the optical density of said sites,
wherein said photodetectors are divided into blocks, each consisting of a plurality of photodetectors, in such a way that photodetectors in said blocks are spaced substantially apart on said detector board, and the outputs of the photodetectors of each said block are connected together to yield a common output signal, whereby the output of a selected photodetector can be analyzed by selecting the common output signal for the block in which the photodetector lies.

25. A measurement system as in claim 24 wherein said means for imparting mixing movement to said samples comprises means for imparting movement to said assay plate.

26. A measurement device as in claims 24, or 25 wherein said light source provides ultraviolet light.

27. A measurement device as in claim 24 wherein each of said blocks comprises 6 photodetectors.

28. A measurement device as in claim 24 wherein said means for analyzing further comprises means for analyzing that portion of said analog signal which is modulated at a predetermined rate.

29. A measurement device as in claims 13 or 20 wherein said means for amplifying comprises:
a amplifier means for receiving said analog signals and providing an amplified output signal;
means for comparing the digital value provided by said analog to digital converter means in response to said amplified output signal with the maximum possible value of said analog to digital converter means; and
means for adjusting the gain of said amplifier means to the maximum gain possible without exceeding the maximum possible value of said analog to digital converter means.

30. A measurement device as in claim 29 wherein said amplifier means comprises:
a first amplifier having a gain set in response to a light signal in the absense of a sample; and
a second amplifier having a gain set in response to a light signal passing through a sample.

* * * * *